(12) United States Patent
Hibino et al.

(10) Patent No.: US 8,638,091 B2
(45) Date of Patent: Jan. 28, 2014

(54) ROTARY EDDY CURRENT TESTING PROBE DEVICE

(75) Inventors: Takashi Hibino, Narita (JP); Takashi Fujimoto, Narita (JP); Shigeki Namekata, Narita (JP); Keisuke Komatsu, Narita (JP); Yoshiyuki Nakao, Osaka (JP); Makoto Takata, Osaka (JP); Makoto Sakamoto, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 167 days.

(21) Appl. No.: 13/286,429

(22) Filed: Nov. 1, 2011

(65) Prior Publication Data

US 2012/0092005 A1  Apr. 19, 2012

Related U.S. Application Data

(63) Continuation of application No. PCT/JP2010/058330, filed on May 18, 2010.

(30) Foreign Application Priority Data

May 22, 2009  (JP) ................................ 2009-123646

(51) Int. Cl.
    *G01N 27/90*  (2006.01)
(52) U.S. Cl.
    USPC ............................. 324/242; 324/239; 324/240
(58) Field of Classification Search
    USPC ......................................... 324/239, 240, 242
    See application file for complete search history.

(56) References Cited

U.S. PATENT DOCUMENTS 6,310,476 B1 * 10/2001 Kawanami et al. ........... 324/241

FOREIGN PATENT DOCUMENTS

| JP | 53-28467 | 7/1978 |
|---|---|---|
| JP | 07-34366 | 6/1995 |
| JP | 10-111279 | 4/1998 |
| JP | 10-197493 | 7/1998 |
| JP | 2007-248169 | 9/2007 |
| JP | 2007-263930 | 10/2007 |
| JP | 2008-241285 | 10/2008 |

\* cited by examiner

*Primary Examiner* — Reena Aurora
(74) *Attorney, Agent, or Firm* — Clark & Brody

(57) ABSTRACT

A rotary eddy current flaw detection probe device has a plurality of Θ-shaped eddy current flaw detection probes attached in a rotating disc for detecting flaws in all directions regardless of the flaw direction. Four Θ-shaped eddy current testing probes P11 to P22 are arranged around the rotation center Ds1 of a rotating disc 111 and are embedded in the disc 111. The coil planes of detector coils Ds11 to Ds22 of the testing probes P11 to P22 are parallel with each other, and are perpendicular to the rotation plane of the rotating disc 111. The coil planes of the detector coils incline at an angle θ relative to a line Y passing through the centers Ps11 and Ps12 of the probes P11 and P12. The detector coils Dc11 and Dc12 are cumulatively connected to each other and the detector coils Dc21 and Dc22 are differentially connected to each other.

5 Claims, 6 Drawing Sheets

Fig.1A1
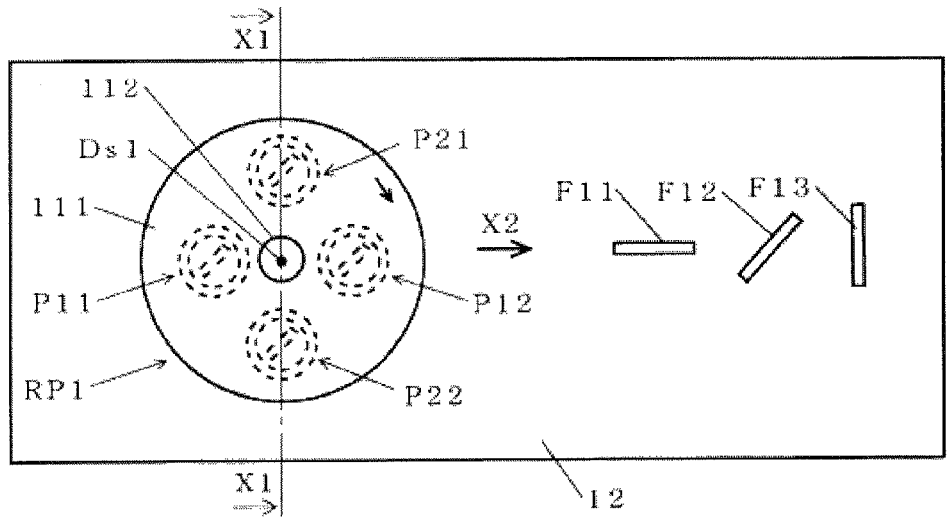
Fig.1A2
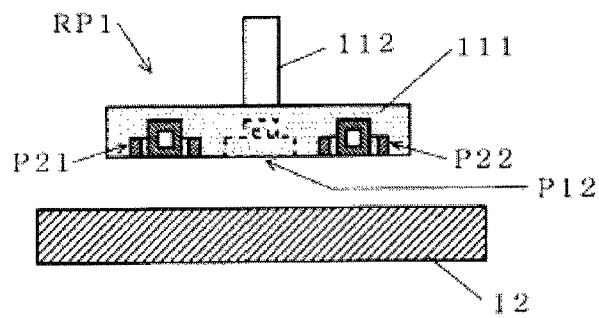
Fig.1B1
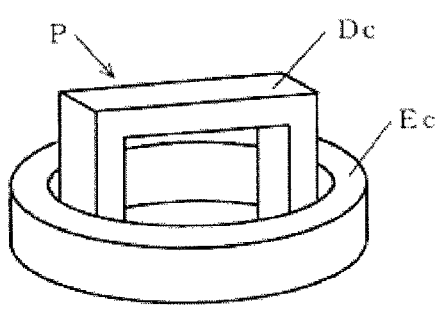
Fig.1B2
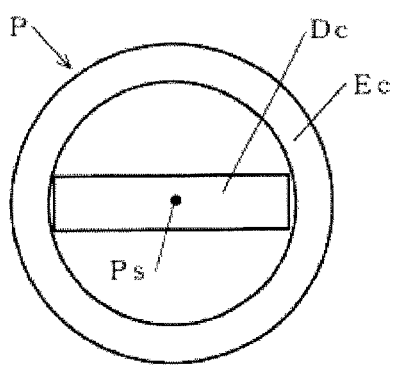

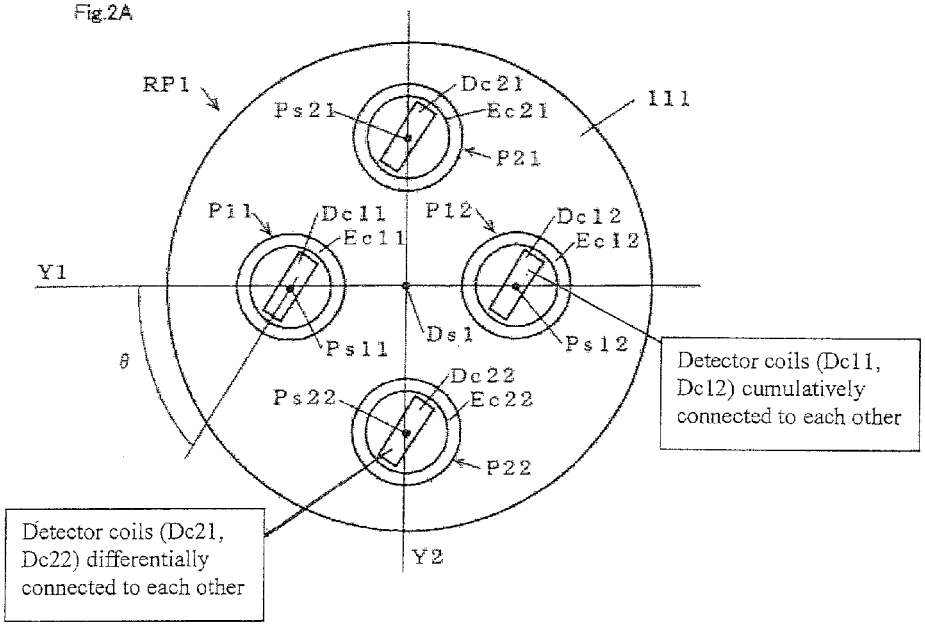
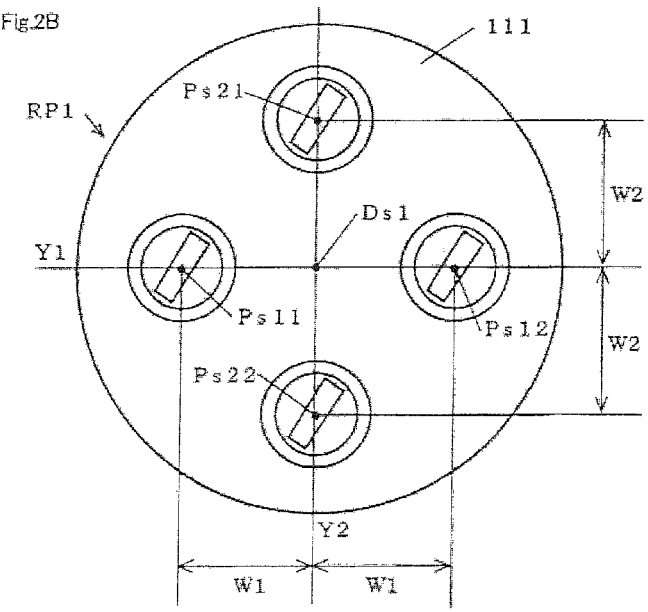

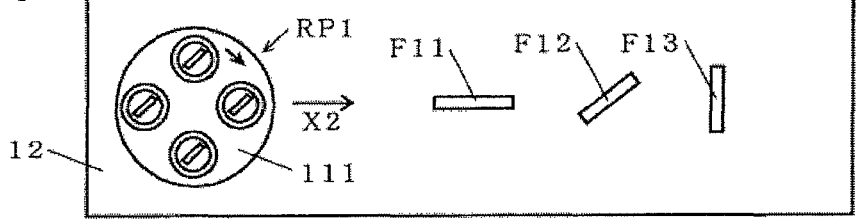
Fig.3A1
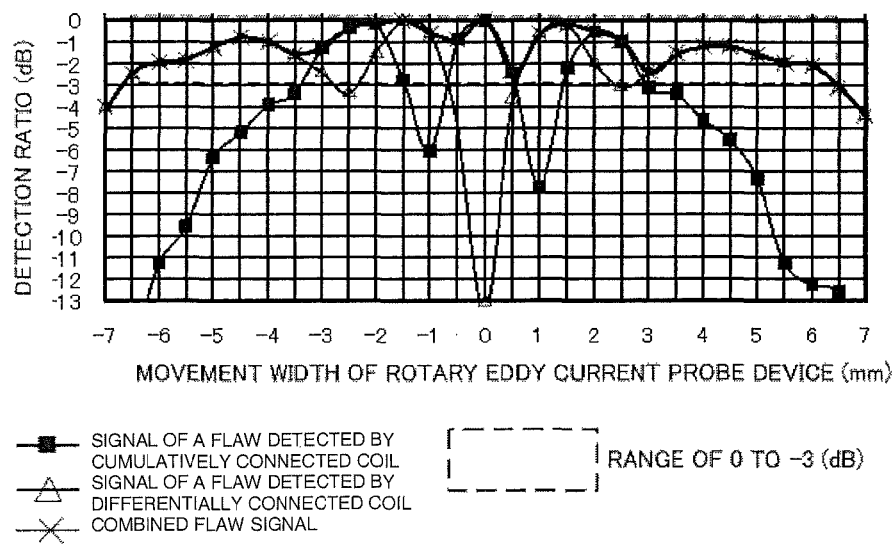
Fig.3A2
- ■ SIGNAL OF A FLAW DETECTED BY CUMULATIVELY CONNECTED COIL
- △ SIGNAL OF A FLAW DETECTED BY DIFFERENTIALLY CONNECTED COIL
- × COMBINED FLAW SIGNAL
[ ] RANGE OF 0 TO −3 (dB)
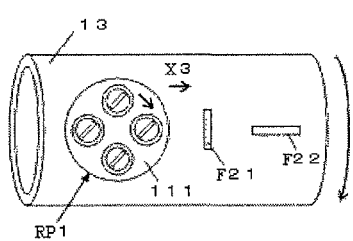
Fig.3B1
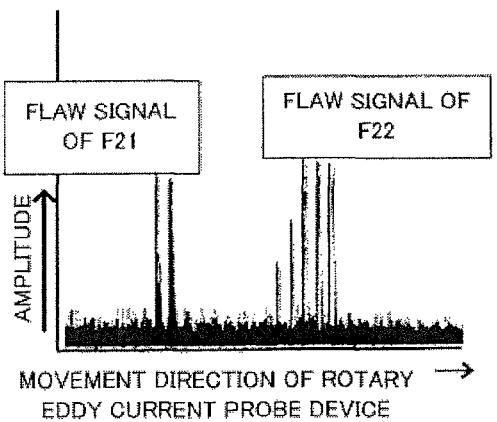
Fig.3B2

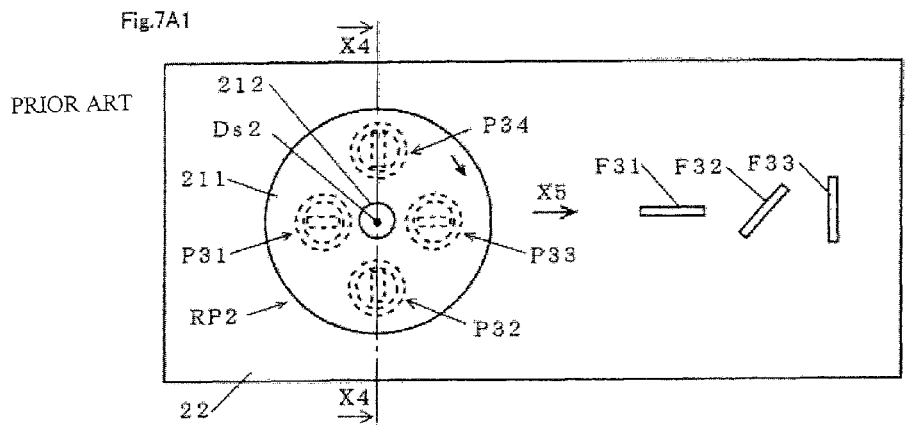
Fig.7A1 PRIOR ART
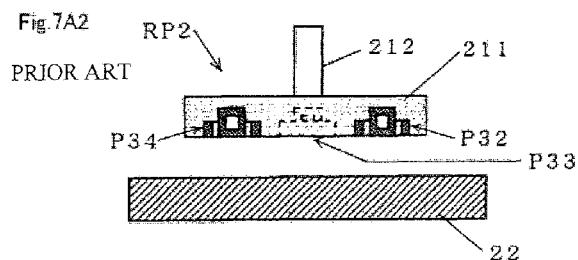
Fig.7A2 PRIOR ART
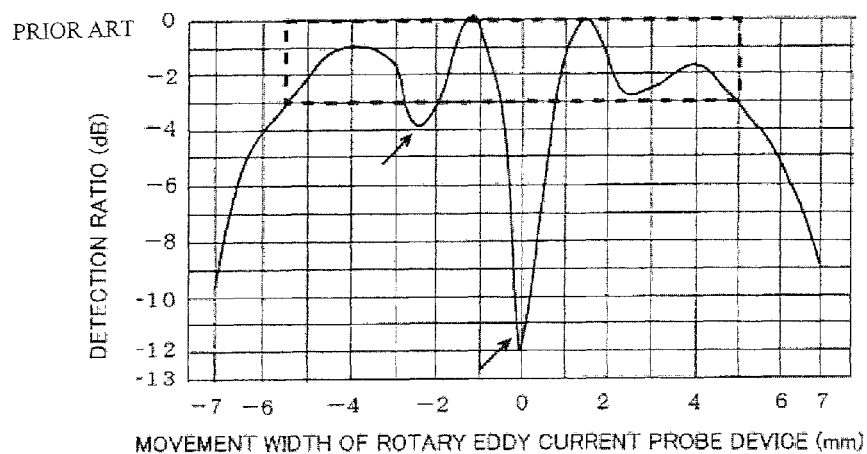
Fig.7B PRIOR ART

US 8,638,091 B2

ROTARY EDDY CURRENT TESTING PROBE DEVICE

TECHNICAL FIELD

The present invention relates to a rotary eddy current testing probe device for detecting flaws by rotating and moving a rotating disc (to scan) to which a plurality of eddy current testing probes are attached.

BACKGROUND ART

There has conventionally been proposed an rotary eddy current testing probe device for detecting flaws in all directions in an electric conductor such as a metal by rotating and moving a rotating disc to which a plurality of eddy current testing probes are attached (for example, refer to JP2007-248169A).

In this description, an eddy current testing probe is referred to as an eddy current probe, and a device including a rotating disc to which a plurality of eddy current testing probes are attached is referred to as a rotary eddy current testing probe device. The rotary eddy current testing probe device is abbreviated to a rotary eddy current probe device as appropriate.

A coil axis means an axis that is the center of spiral winding of windings constituting a coil, and a coil plane means a plane perpendicular to the coil axis.

A conventional rotary eddy current probe device including four eddy current probes attached to a rotating disc will be described with reference to FIGS. 7A1, 7A2 and 7B.

FIG. 7A1 is a plan view of the rotary eddy current probe device and an object being inspected, FIG. 7A2 is a sectional view taken along the line X4-X4 of FIG. 7A1, and FIG. 7B is a graph showing the amplitude characteristic of a flaw signal detected by the rotary eddy current probe device.

A rotary eddy current probe device RP2 has four Θ-shaped eddy current probes P31 to P34 and a rotating disc 211. The eddy current probes P31 to P34 are embedded in the rotating disc 211 by molding, and are arranged so as to face the inspection surface of an object being inspected 22 for which the presence of a flaw is inspected. The Θ-shaped eddy current probe has an exciting coil for exciting an eddy current in the object being inspected and a detector coil disposed on the inside of the exciting coil to detect the eddy current excited in the object being inspected, and both the coils are arranged so that the respective coil planes are perpendicular to each other. That is, the coil plane of the exciting coil is parallel with the rotation plane of the rotating disc 211, and the coil plane of the detector coil is perpendicular to the rotation plane of the rotating disc 211. The rotating disc 211 is rotated by the rotation of a rotating shaft 212, and the rotating shaft 212 is rotated by a motor (not shown).

The four eddy current probes P31 to P34 are arranged at approximately equal intervals (intervals of 90 degrees) in order in the circumferential direction around the rotation center Ds2. Of the four eddy current probes P31 to P34, the eddy current probes P31 and P33 are located on opposite sides with respect to the rotation center Ds2, and the eddy current probes P32 and P34 are also located on opposite sides with respect to the rotation center Ds2. That is, the four eddy current probes P31 to P34 are composed of two sets: a set of the eddy current probes P31 and P33 and a set of the eddy current probes P32 and P34. One set of the detector coils and the other set of the detector coils are arranged so that the coil planes are perpendicular to each other and the coil axes are also perpendicular to each other.

The following is an explanation of a flaw signal detected when the object being inspected 22 shown in FIG. 7A1 is inspected by using the rotary eddy current probe device RP2.

On the inspection surface of the object being inspected 22, a flaw F31 elongated in parallel with the movement direction (X5 direction) of the rotary eddy current probe device RP2, a flaw F32 slantwise intersecting with the movement direction, and a flaw F33 intersecting at right angles with the movement direction are formed. All of the flaws F31, F32 and F33 each have a length (length of the long side) of 150 mm, a width (width of the short side) of 0.5 mm, and a depth of 0.3 mm.

The rotary eddy current probe device RP2 excites an eddy current in the object being inspected by using the exciting coil, detects the eddy current excited in the object being inspected by using the detector coil, and detects a flaw on the basis of a signal detected by the detector coil. The four detector coils are cumulatively connected. The signal detected by the detector coil is referred to as a flaw signal.

When the rotary eddy current probe device RP2 is moved in the X5 direction along the inspection surface of the object being inspected 22 while being rotated, a flaw signal caused by the flaws F31 and F32 can be detected, but a flaw signal caused by the flaw F33 cannot be detected sufficiently. That is, the flaw signal caused by the flaw F33 is as shown in FIG. 7B. In FIG. 7B, the ordinate represents the detection ratio that is the ratio of the amplitude of the signal of a detected flaw to the maximum amplitude, and the abscissa represents the movement width in the X5 direction of the rotary eddy current probe device RP2. The zero point on the abscissa corresponds to a position at the time when the rotation center Ds2 of the rotary eddy current probe device RP2 moves to just above the flaw F33. The rectangle drawn by a broken line in FIG. 7B indicates the range in which the detection ratio of flaw signal is −3 dB or more in front and rear of the flaw F33 and the range of the movement width of rotary eddy current probe device capable of detecting the flaw. The detection ratio of −3 dB is a signal detection ratio that is generally thought to be effective for flaw detection, and when the detection ratio is −3 dB or more, it is judged that a flaw is present.

In the case of FIG. 7B, despite the presence of flaw, the detection ratio of flaw signal is less than −3 dB at two locations indicated by arrows in the figure, which reveals the presence of a region in which the flaw signal is difficult to detect.

DISCLOSURE OF THE INVENTION

The conventional rotary eddy current probe device has difficulty in detecting a flaw intersecting at right angles with the movement direction of the rotary eddy current probe device as described above, so that the detecting capacity of the conventional rotary eddy current probe device is insufficient as a rotary eddy current probe device for detecting flaws in all directions.

The present invention has been made in view of the above circumstances, and accordingly an object thereof is to provide a rotary eddy current probe device capable of detecting flaws in all directions including a flaw intersecting at right angles with the movement direction thereof.

To achieve the above object, the present invention provides a rotary eddy current testing probe device for detecting flaws on an object being inspected, including a rotating disc (111); and four Θ-shaped eddy current testing probes (P11, P21, P12, P22) attached at approximately equal intervals in the circumferential direction around a rotation center (Ds1) of the rotating disc (111), wherein the four eddy current testing probes (P11, P21, P12, P22) are composed of two sets of the eddy current testing probes, each one set including two eddy current testing probes located on opposite sides with respect to a rotation center (Ds1), and the four eddy current testing probes have exciting coils (Ec11, Ec21, Ec12, Ec22) for exciting a current in the object being inspected, and detector coils (Dc11, Dc21, Dc12, Dc22) for detecting the current exited in the object being inspected; the coil planes of the exciting coils (Ec11, Ec21, Ec12, Ec22) are parallel with the rotation plane of the rotating disc; the coil planes of the detector coils (Dc11, Dc21, Dc12, Dc22) are perpendicular to the rotation plane of the rotating disc; the coil planes of the detector coils (Dc11, Dc21, Dc12, Dc22) are parallel with each other, and incline at a predetermined angle (θ) relative to a line (Y1) passing through the respective centers of two eddy current testing probes of one set of the two-set eddy current testing probes; and the two detector coils (Dc11, Dc12) of the one set of eddy current testing probes are cumulatively connected to each other, and the two detector coils (Dc21, Dc22) of the other set of eddy current testing probes are differentially connected to each other.

According to the present invention, the rotary eddy current testing probe device can detect flaws in all directions without omission regardless of the direction of flaw on the object being inspected. The rotary eddy current testing probe device of the present invention can detect flaws in a wider range in one movement (i.e. scan) of the rotary eddy current probe device: the testing range of the conventional rotary eddy current testing probe device is about 2 mm, whereas the testing range of the rotary eddy current testing probe device of the present invention is 10 mm or wider. Therefore, the rotary eddy current testing probe device of the present invention can detect flaws in a wide range by one flaw detection, so that the testing time can be shortened.

Preferably, the predetermined angle (θ) is 15 to 60 degrees, most favorably being 45 degrees. By setting the inclination angle (θ) of the coil plane of the detector coil at the above-described value, variations in flaw signals caused by the flaw direction can be reduced.

Preferably, the ratio (W1:W2) of a distance (W1) from a center (Ps11, Ps12) of respective eddy current testing probes of one set to a rotation center (Ds1) of the rotating disc to a distance (W2) from a center (Ps21, Ps22) of respective eddy current testing probes of the other set to the rotation center (Ds1) of the rotating disc is 1:1 to 1:3. By setting the ratio (W1:W2) in the range of 1:1 to 1:3, variations in flaw signals caused by the flaw direction can be reduced further.

Preferably, in the case where the inspection surface of the object being inspected has a curvature, the ratio (W1:W2) is 1:1.75. By setting the ratio (W1:W2) at 1:1.75, flaws on the inspection surface of the object being inspected having a curvature can be detected.

BRIEF DESCRIPTION OF THE DRAWINGS

FIGS. 1A1, 1A2, 1B1 and 1B2 are schematic views showing the configuration of a rotary eddy current probe device in accordance with an embodiment of the present invention;

FIGS. 2A and 2B are explanatory views showing the positional relationship of eddy current probes of the rotary eddy current probe device shown in FIG. 1;

FIGS. 3A1, 3A2, 3B1 and 3B2 are explanatory views for explaining flaw signals detected by the rotary eddy current probe device shown in FIG. 1;

FIGS. 7A1, 7A2 and 7B are schematic views showing the configuration of a conventional rotary eddy current probe device.

BEST MODE FOR CARRYING OUT THE INVENTION

Figure 4:
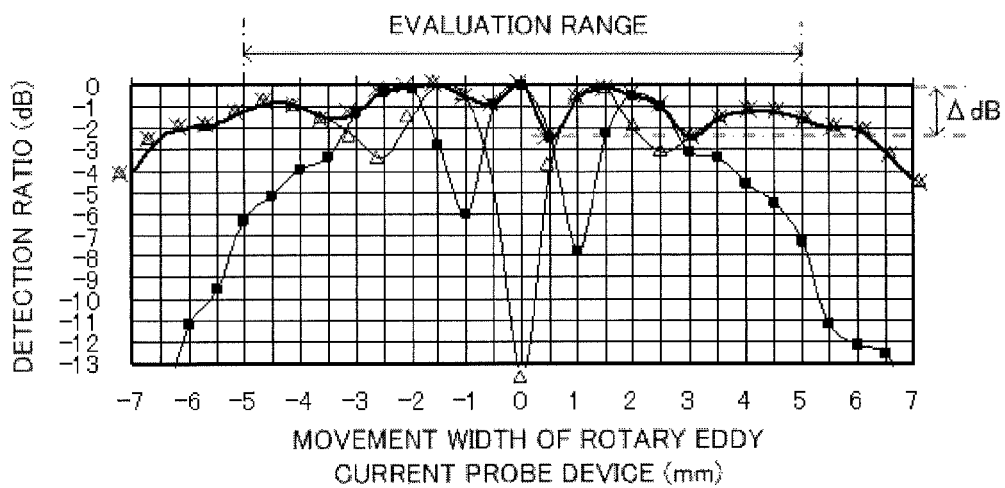
FIG. 4 is a graph for explaining ΔdB.

A rotary eddy current probe device in accordance with an embodiment of the present invention will now be described with reference to FIGS. 1 to 3.

First, FIGS. 1A1, 1A2, 1B1 and 1B2 are explained.

FIG. 1A1 is a plan view of the rotary eddy current probe device and an object being inspected, FIG. 1A2 is a sectional view taken along the line X1-X1 of FIG. 1A1, FIG. 1B1 is a perspective view of a Θ-shaped eddy current probe, and FIG. 1B2 is a plan view of the Θ-shaped eddy current probe.

The rotary eddy current probe device RP1 has four Θ-shaped eddy current probes P11, P21, P12 and P22 (hereinafter, P is sometimes used as the general symbol for P11, P21, P12 and P22) and a rotating disc 111. The eddy current probes P11, P21, P12 and P22 are embedded in the rotating disc 111 by molding, and are arranged so as to face the inspection surface of the object being inspected 12 for which the presence of a flaw is inspected. The rotating disc 111 is rotated by the rotation of a rotating shaft 112, and the rotating shaft 112 is rotated by a motor (not shown). The Θ-shaped eddy current probe P has an exciting coil Ec for exciting an eddy current in the object being inspected and a detector coil Dc disposed on the inside of the exciting coil Ec to detect the eddy current excited in the object being inspected, and both the coils are arranged so that the respective coil planes are perpendicular to each other. That is, the coil plane of the exciting coil Ec is parallel with the rotation plane of the rotating disc 111, and the coil plane of the detector coil Dc is perpendicular to the rotation plane of the rotating disc 111.

The rotary eddy current probe device RP1 excites an eddy current in the object being inspected by using the exciting coil, detects the eddy current excited in the object being inspected by the detector coil, and detects a flaw on the basis of a signal detected by the detector coil. The signal detected by the detector coil is referred to as a flaw signal.

Instead of being embedded in the rotating disc 111, the eddy current probe P may be fitted in an opening for allowing the eddy current probe P to be fitted in, which is formed in a disc formed by a plate-shaped body, or may be attached to the rotating disc 111 by using fittings. Therefore, when reference is made to "the eddy current probe P is attached to the rotating disc 111" in this description, it includes how the eddy current probe P is embedded in the rotating disc 111.

The symbol Ps in FIG. 1B2 denotes the center of the exciting coil Ec.

The four eddy current probes P11, P21, P12 and P22 are arranged at approximately equal intervals (intervals of 90 degrees) in order in the circumferential direction around the rotation center Ds1 of the rotary eddy current probe device RP1. Of the four eddy current probes P11, P21, P12 and P22, the eddy current probes P11 and P12 are located on opposite sides with respect to the rotation center Ds1, and the eddy current probes P21 and P22 are also located on opposite sides with respect to the rotation center Ds1. That is, the four eddy current probes P11, P21, P12 and P22 are composed of two sets: a set of the eddy current probes P11 and P12 and a set of the eddy current probes P21 and P22.

The respective detector coils of the eddy current probes P11 and P12 are cumulatively connected, and the respective detector coils of the eddy current probes P21 and P22 are differentially connected. The cumulative connection means a way of connection in which the current directions of two coils are the same. For example, when the winding directions of two coils are the same, the winding end of one coil and the winding start of the other coil are connected to each other, and when the winding directions of two coils are reverse, the winding end of one coil and the winding end of the other coil are connected to each other. The differential connection means a way of connection in which the current directions of two coils are reverse. For example, when the winding directions of two coils are the same, the winding start of one coil and the winding start of the other coil are connected to each other, and when the winding directions of two coils are reverse, the winding end of one coil and the winding start of the other coil are connected to each other.

On the inspection surface of the object being inspected 12, a flaw F11 elongated in parallel with the movement direction (X2 direction) of the rotary eddy current probe device RP1, a flaw F12 slantwise intersecting with the movement direction, and a flaw F13 intersecting at right angles with the movement direction are formed.

Next, the positional relationship of the four eddy current probes P of the rotary eddy current probe device RP1 shown in FIGS. 1A1, 1A2, 1B1 and 1B2 is described with reference to FIGS. 2A and 2B.

First, FIG. 2A is explained.

The eddy current probes P11 and P12 are located on opposite sides with respect to the rotation center of the rotary eddy current probe device (the rotation center of the rotating disc) Ds1, and the centers of both the eddy current probes (the centers of exciting coils Ec11 and Ec12) Ps11 and Ps12 are arranged on a line Y1 drawn through the rotation center Ds1. Similarly, the eddy current probes P21 and P22 are located on opposite sides with respect to the rotation center of the rotary eddy current probe device (the rotation center of the rotating disc) Ds1, and the centers of both the eddy current probes (the centers of exciting coils Ec21 and Ec22) Ps21 and Ps22 are arranged on a line Y2 drawn through the rotation center Ds1. The lines Y1 and Y2 intersect at right angles with each other. Therefore, the four eddy current probes P11, P21, P12 and P22 are arranged at approximately equal intervals (intervals of 90 degrees) in the circumferential direction around the rotation center Ds1.

The detector coils Dc11, Dc21, Dc12 and Dc22 of the four eddy current probes P11, P21, P12 and P22 are arranged so that the respective coil planes thereof are parallel with each other. The coil planes of the detector coils Dc11 and Dc12 are arranged so as to incline at a predetermined angle θ relative to the line Y1 passing through the centers Ps11 and Ps12 of the eddy current probes P11 and P12 (hereinafter, the angle between the coil plane of the detector coil Dc11, Dc12 and the line Y1 passing through the centers Ps11 and Ps12 of the eddy current probes P11 and P12 is referred to as a probe angle). In this case, the coil planes of the detector coils Dc21 and Dc22 also incline at the angle θ relative to the line Y1 because these coil planes are parallel with the coil planes of the detector coils Dc11 and Dc12. The inclination angles of respective coil planes of the four detector coils Dc11, Dc21, Dc12 and Dc22 may be determined with the line Y2 passing through the centers Ps21 and Ps22 of the eddy current probes P21 and P22 being a reference line.

The reason why the detector coils are arranged incliningly so that the probe angle is θ is explained.

For the eddy current probe, when a flaw parallel with the detector coil plane passes under the lower surface of detector coil, a flaw signal is generated. The rotary eddy current probe device in which the detector coil planes are radial from the center of the rotary eddy current probe device to the periphery as in the prior art can also detect flaws in all directions. However, in the case where the object being inspected is a steel pipe or tube, a gap between the detector coil and the flaw on the surface of steel pipe or tube (referred to as a liftoff) increases when the detector coil passes above a flaw in the pipe or tube circumferential direction as compared with the time when the detector coil passes above a flaw in the pipe or tube axis direction, so that a difference occurs in the magnitude of flaw signal.

In contrast, in the present invention, by providing a predetermined angle, the gap between a flaw in the pipe or tube axis direction and the detector coil plane and the gap between a flaw in the pipe or tube circumferential direction and the detector coil plane can be made equal to each other, so that the difference in the magnitude of flaw signal can be decreased.

The probe angle θ can be set in the range of 0 to 90 degrees. However, the probe angle θ is set preferably in the range of 15 to 60 degrees, further preferably at 45 degrees. The details thereof will be described later.

Next, FIG. 2B is explained.

FIG. 2B is an explanatory view for explaining how the distances of the four eddy current probes from the rotation center Ds1 in the rotary eddy current probe device shown in FIG. 2A may be set. The symbols of the eddy current probes, the exciting coils, and the detector coils are the same as those in FIG. 2A, and therefore these symbols are omitted in FIG. 2B.

For the set of the eddy current probes P11 and P12, the distances from the rotation center Ds1 to the centers Ps11 and Ps12 of respective eddy current probes are set at W1, and for the set of the eddy current probes P21 and P22, the distances from the rotation center Ds1 to the centers Ps21 and Ps22 of respective eddy current probes are set at W2. The distances W1 and W2 are set, for example, at 4.2 mm and 7.2 mm, respectively. The ratio (W1:W2) between the distances W1 and W2 can be set at 1:n (n=1 or more). However, in the case where the object being inspected is of a flat plate shape, the ratio of 1:1 to 1:3 is preferable, and in the case where the object being inspected is of a tubular shape and the inspection surface thereof has a curvature, the ratio of near 1:1.75 is preferable. The details thereof will be described later. For the connection of detector coils of the eddy current probes P, in the case where the distance W1 is longer than the distance W2, the respective detector coils of the eddy current probes P11 and P12 are differentially connected, and the respective detector coils of the eddy current probes P21 and P22 are cumulatively connected.

FIGS. 3A1, 3A2, 3B1 and 3B2 show the experimental results of the rotary eddy current probe device in accordance with the embodiment of the present invention.

FIGS. 3A1 and 3A2 show the case where the object being inspected is of a flat plate shape, and FIGS. 3B1 and 3B2 show the case where the object being inspected is of a tubular shape. The probe angle θ in FIG. 2A of the rotary eddy current probe device RP1 was set at 45 degrees, and the distances W1 and W2 shown in FIG. 2B were set at 4.2 mm and 7.2 mm, respectively.

First, FIGS. 3A1 and 3A2 are explained.

In FIG. 3A1, the object being inspected 12 was of a plate shape, and on the inspection surface thereof, a flaw F11 elongated in parallel with the movement direction (X2 direction) of the rotary eddy current probe device RP1, a flaw F12 slantwise intersecting with the movement direction, and a flaw F13 intersecting at right angles with the movement direction were formed. All of the flaws F11, F12 and F13 each had a length (length of the long side) of 150 mm, a width (width of the short side) of 0.5 mm, and a depth of 0.3 mm. The rotating disc 111 of the rotary eddy current probe device RP1 had a diameter of 35 mm. The exciting coil was formed by winding a conductor having a wire diameter of 0.16 mm 180 turns, and the external shape thereof was a circular shape of 4 mm (length)×4 mm (width)×2.5 mm (height). The detector coil was formed by winding a conductor having a wire diameter of 0.05 mm 120 turns, and the external shape thereof was a rectangular shape of 3.3 mm (length)×4 mm (width)×1.5 mm (height).

In order to test a pipe or tube, the rotary eddy current probe device RP1 was moved in the X2 direction while being rotated at 5000 rpm, and data were captured at intervals of 0.5 mm.

Of the signals of flaws detected by the rotary eddy current probe device RP1, the flaw signal generated by the flaw F13 had amplitude characteristics shown in FIG. 3A2. In FIG. 3A2, the ordinate represents the detection ratio that is the ratio of the amplitude of the signal of a detected flaw to the maximum amplitude, and the abscissa represents the movement width in the X2 direction of the rotary eddy current probe device RP1. A broken line in FIG. 3A2 indicates the range in which the detection ratio of flaw signal is 0 to −3 dB and the range of the movement width of rotary eddy current probe device capable of detecting the flaw. The zero point on the abscissa corresponds to a position at the time when the rotation center Ds1 of the rotary eddy current probe device RP1 moves to just above the flaw F13. The graph indicated by plots of black rectangular shape shows a flaw signal detected by the cumulatively connected detector coil, the graph indicated by plots of white triangular shape shows a flaw signal detected by the differentially connected detector coil, and the graph indicated by plots of x shows a combined flaw signal represented by taking out the flaw signal having a larger detection ratio from the signal of a flaw detected by the cumulatively connected detector coil and the signal of a flaw detected by the differentially connected detector coil. By the use of the flaw signal having a larger detection ratio of the signal of a flaw detected by the cumulatively connected detector coil and the signal of a flaw detected by the differentially connected detector coil, flaws can be detected in the range of detection ratio of 0 to −3 dB, so that a flaw such as the flaw F13 that has been difficult to detect by using the conventional rotary eddy current probe device can be detected. That is, flaws in all directions can be detected without omission.

Thus, in the differential connection, a "valley" portion in which the detection level decreases is produced in a location near the center of the flaw passing-through position. Therefore, as a means for compensating this "valley" portion, a "peak" is formed by cumulatively connecting one set of the detector coils, whereby a region effective for flaw detection can be widened by using outputs of two sets of detector coils.

The combined flaw signal may be taken out the sum of the flaw signals, which is obtained by adding the amplitude of the signal of a flaw detected by the cumulatively connected detector coils and the amplitude of the flaw signals detected by the differentially connected detector coils.

Figure 5:
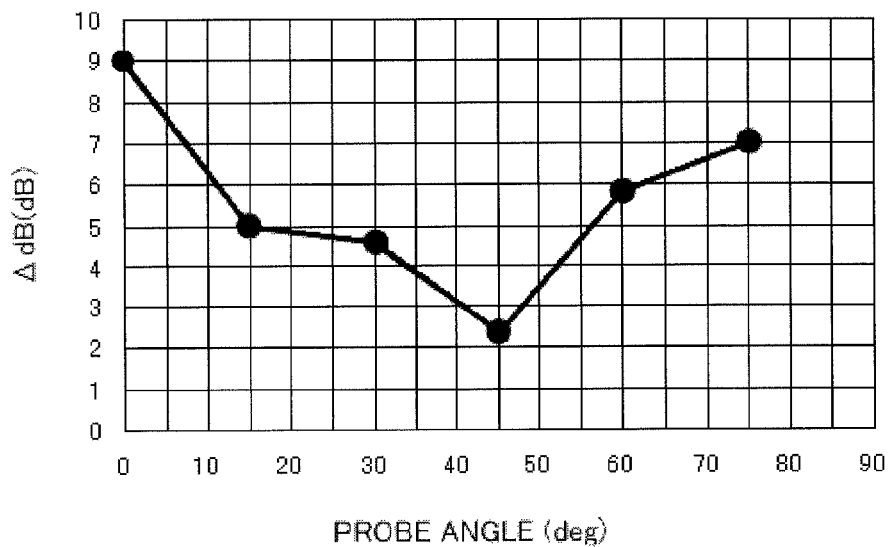
FIG. 5 is a graph showing the relationship between a probe angle and ΔdB.

Next, the probe angle is explained. As shown in FIG. 4, the absolute value of dB at a point at which the detection ratio of the combined flaw signal is the lowest in the range of movement width of rotary eddy current probe device of −5 mm to 5 mm is taken as ΔdB. The value of ΔdB is as small as possible. FIG. 5 shows the relationship between the probe angle and ΔdB. As shown in FIG. 5, in the probe angle range of 15 to 60 degrees, ΔdB exhibits a favorable value, and the value of ΔdB is most favorable when the probe angle is near 45 degrees.

Next, the ratio (W1:W2) between the distances W1 and W2 in the case where the object being inspected is of a tubular shape or a plate shape. When the ratio (W1:W2) between the distances W1 and W2 is changed, the value of ΔdB changes as in the case where the probe angle is changed.

Figure 6A:
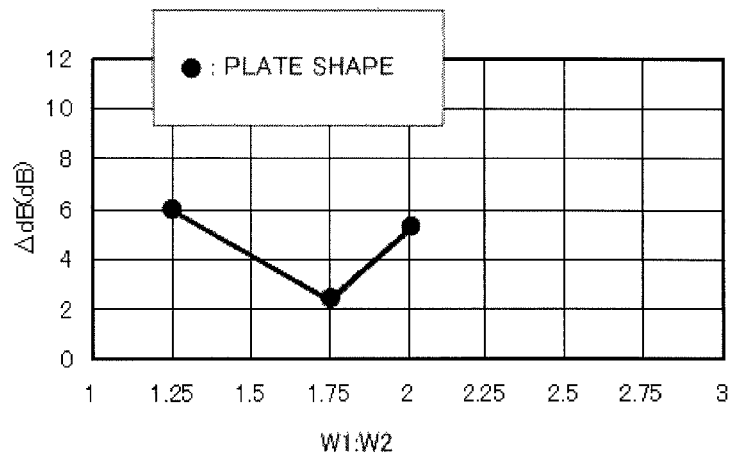
FIGS. 6A and 6B are graphs showing the relationship between a distance ratio of W1 to W2 (W1:W2) and ΔdB.
Figure 6B:
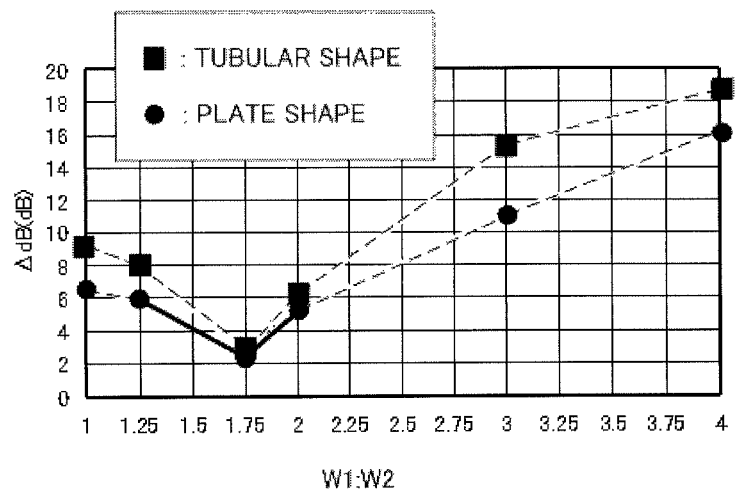

FIGS. 6A and 6B show the relationship between the ratio (W1:W2) between the distances W1 and W2 and ΔdB. FIG. 6A shows experimental data, and FIG. 6B shows the experimental data plus simulation results.

As shown in FIGS. 6A and 6B, ΔdB exhibits a good value in the W1:W2 range of 1:1 to 1:3, and takes the most favorable value near the W1:W2 range of 1:1.75, in the case where the object being inspected is of a tubular shape or a plate shape. The ΔdB in the W1:W2 range of 1:1.75 falls greatly relative to the other W1:W2 range, so that, in particular, in the case where the object being inspected is of a tubular shape, ΔdB takes the most favorable value near the W1:W2 range of 1:1.75.

Next, FIGS. 3B1 and 3B2 are explained.

In FIG. 3B1, the object being inspected 13 was a tubular-shaped body having a diameter of 73 mm, and on the inspection surface thereof, a flaw F21 elongated in the circumferential direction of the object being inspected 13 and a flaw F22 elongated in the pipe or tube axis direction of the object being inspected 13 were formed. The flaws F21 and F22 each had a length (length of the long side) of 25 mm, a width (width of the short side) of 1 mm, and a depth of 0.3 mm.

In order to test a pipe or tube, the rotary eddy current probe device RP1 was moved 10 mm in the pipe or tube axis direction (X3 direction) every one turn of the object being inspected 13 while the rotary eddy current probe device RP1 was rotated at 5000 rpm and the object being inspected 13 was rotated at 1000 mm/s.

The signal of a flaw detected by the rotary eddy current probe device RP1 becomes as shown in FIG. 3B2, and the rotary eddy current probe device RP1 can detect the flaw signals caused by the flaws F21 and F22. In FIG. 3B2, the ordinate represents the amplitude of flaw signal, and the abscissa represents the movement direction of the rotary eddy current probe device RP1.

FIG. 3B2 reveals that even if the object being inspected is of a tubular shape, the rotary eddy current probe device RP1 can detect flaws in all direction.

The invention claimed is:

1. A rotary eddy current testing probe device for detecting flaws on an object being inspected, comprising:
   a rotating disc (111); and
   four eddy current testing probes (P11, P21, P12, P22) attached at approximately equal intervals in a circumferential direction around a rotation center (Ds1) of the rotating disc (111), wherein
   the four eddy current testing probes (P11, P21, P12, P22) are composed of two sets of the eddy current testing probes, each one set including two eddy current testing probes located on opposite sides with respect to a rotation center (Ds1), and each of the four eddy current testing probes has a circular exciting coils (Ec11, Ec21, Ec12, Ec22) for exciting a current in the object being inspected, and a rectangular detector coils (Dc11, Dc21, Dc12, Dc22) disposed on an inside of the exciting coil for detecting the current exited in the object being inspected;
   coil planes of the exciting coils (Ec11, Ec21, Ec12, Ec22) are parallel with a rotation plane of the rotating disc;

coil planes of the detector coils (Dc11, Dc21, Dc12, Dc22) are perpendicular to the rotation plane of the rotating disc;

the coil planes of the four detector coils (Dc11, Dc21, Dc12, Dc22) are parallel with each other, and incline at a predetermined angle ($\theta$) relative to a line (Y1) passing through the respective centers of two eddy current testing probes of one set of the two-set eddy current testing probes; and the two detector coils (Dc11, Dc12) of the one set of eddy current testing probes are cumulatively connected to each other, and the two detector coils (Dc21, Dc22) of the other set of eddy current testing probes are differentially connected to each other.

2. The rotary eddy current testing probe device according to claim 1, wherein the predetermined angle ($\theta$) is 15 to 60 degrees.

3. The rotary eddy current testing probe device according to claim 1, wherein a ratio (W1:W2) of a distance (W1) from a center (Ps11, Ps12) of respective eddy current testing probes of one set to a rotation center (Ds1) of the rotating disc to a distance (W2) from a center (Ps21, Ps22) of respective eddy current testing probes of the other set to the rotation center (Ds1) of the rotating disc is 1:1 to 1:3.

4. The rotary eddy current testing probe device according to claim 3, wherein in the case where an inspection surface of the object being inspected has a curvature, the ratio (W1:W2) is 1:1.75.

5. The rotary eddy current testing probe device according to claim 1, wherein the predetermined angle ($\theta$) is 45 degrees.

* * * * *